United States Patent
Balakrishnan et al.

(10) Patent No.: US 9,501,049 B2
(45) Date of Patent: Nov. 22, 2016

(54) DYNAMIC ENVIRONMENT ADAPTATION

(71) Applicant: FUJITSU LIMITED, Kawasaki-shi, Kanagawa (JP)

(72) Inventors: Rajalakshmi Balakrishnan, Santa Clara, CA (US); Ajay Chander, San Francisco, CA (US)

(73) Assignee: FUJITSU LIMITED, Kawasaki (JP)

( * ) Notice: Subject to any disclaimer, the term of this patent is extended or adjusted under 35 U.S.C. 154(b) by 364 days.

(21) Appl. No.: 14/218,604

(22) Filed: Mar. 18, 2014

(65) Prior Publication Data
US 2015/0268641 A1 Sep. 24, 2015

(51) Int. Cl.
*A61B 5/00* (2006.01)
*G05B 15/02* (2006.01)
*G05D 23/19* (2006.01)

(52) U.S. Cl.
CPC ............ *G05B 15/02* (2013.01); *G05D 23/1917* (2013.01); *A61B 5/0006* (2013.01); *A61B 5/0008* (2013.01); *A61B 2560/0252* (2013.01); *G05B 2219/2614* (2013.01); *G05B 2219/2642* (2013.01)

(58) Field of Classification Search
CPC ............ G05B 15/02; G05B 2219/2614; G05B 2219/2642; A61B 5/0006; A61B 5/0008; A61B 2560/0252; G05D 23/1917
See application file for complete search history.

(56) References Cited

U.S. PATENT DOCUMENTS

| | | | |
|---|---|---|---|
| 9,198,575 B1 * | 12/2015 | Blacutt | A61B 3/113 |
| 2004/0245351 A1 * | 12/2004 | Orfield | F24F 11/006 236/43 |
| 2005/0143617 A1 * | 6/2005 | Auphan | A61B 5/08 600/26 |
| 2008/0114495 A1 * | 5/2008 | Suyama | B60H 1/00642 700/276 |

(Continued)

OTHER PUBLICATIONS

Mohamad-Hoseyn Sigari et al., "A Driver Face Monitoring System for Fatigue and Distraction Detection" International Journal of Vehicular Technology, vol. 2013, Article ID 263983, 11 pages, Nov. 24, 2012.

(Continued)

*Primary Examiner* — Robert Fennema
*Assistant Examiner* — Jennifer L Norton
(74) *Attorney, Agent, or Firm* — Maschoff Brennan

(57) ABSTRACT

A method of dynamically adapting an environment may include collecting sensor data from a biological sensor and an environmental sensor. The method may also include, based on the sensor data, determining whether an optimal environmental state exists in an environment. The optimal environmental state may be defined in a health and wellness policy and may be configured to promote an optimal biological state of an individual in the environment. In response to the optimal environmental state not existing in the environment, the method may include identifying an environmental condition that differs from the optimal environmental state and generating a command configured to alter an operational state of an environmental device that affects the environmental condition.

16 Claims, 6 Drawing Sheets

(56) References Cited

U.S. PATENT DOCUMENTS

| | | | |
|---|---|---|---|
| 2010/0106365 A1* | 4/2010 | Visconti | B60H 1/00742 701/36 |
| 2012/0290266 A1* | 11/2012 | Jain | G06F 19/3406 702/187 |
| 2014/0067130 A1* | 3/2014 | Pillai | H04L 12/2816 700/275 |
| 2014/0207292 A1* | 7/2014 | Ramagem | G05B 15/02 700/278 |
| 2015/0168002 A1* | 6/2015 | Plitkins | F24F 11/0034 165/237 |

OTHER PUBLICATIONS

BeomJin Kang et al., "A Study on the Greenhouse Auto Control System based on Wireless Sensor Network" 2008 International Conference on Security Technology, Dec. 13-15, 2008.
Luis M. Bergasa "Real-Time System for Monitoring Driver Vigilance" IEEE Transactions on Intelligent Transportation Systems, vol. 7, No. 1, Mar. 2006.

* cited by examiner

DYNAMIC ENVIRONMENT ADAPTATION

FIELD

The embodiments discussed herein are related to dynamic environment adaptation.

BACKGROUND

Environments play a significant role in the health and wellness of an individual. Accordingly, an individual may set conditions of the environments to attempt to create an optimal environment for an activity. For example, the environment in which the individual sleeps may affect the quality of rest of the individual. Thus, to best sleep in the environment, the individual may set an ambient temperature to a comfortable level and implement a noise machine to reduce disturbances caused by ambient noise. The ambient temperature and the noise machine may improve the quality of rest of the individual.

To set and/or to adjust a condition of the environments, some device regulators include automated adjustments. For instance, thermostats may sense an ambient temperature and compare the sensed ambient temperature to a set temperature. The thermostat may then adjust a duty cycle of a heating, ventilation, or air-conditioning (HVAC) component based on a difference between the sensed ambient temperature and the set temperature. Similarly, some "smart" thermostats may learn behaviors of the individual and may adjust the duty cycles of an HVAC component based on the learned behaviors. Device regulators having these and similar capabilities may assist in the setting and adjusting of the conditions of the environment. However, the adjustments may be based on a limited number of sensor inputs, may involve periodic action by the individual, and may fail to consider the individual.

The subject matter claimed herein is not limited to embodiments that solve any disadvantages or that operate only in environments such as those described above. Rather, this background is only provided to illustrate one example technology area where some embodiments described herein may be practiced.

SUMMARY

According to an aspect of an embodiment, a method of dynamically adapting an environment may include collecting sensor data from a biological sensor and an environmental sensor. The method may also include, based on the sensor data, determining whether an optimal environmental state exists in an environment. The optimal environmental state may be defined in a health and wellness policy and may be configured to promote an optimal biological state of an individual in the environment. In response to the optimal environmental state not existing in the environment, the method may include identifying an environmental condition that differs from the optimal environmental state and generating a command configured to alter an operational state of an environmental device that affects the environmental condition.

The object and advantages of the embodiments will be realized and achieved at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Some embodiments described herein relate to dynamic environment adaptation. Existing systems operate under a paradigm that an individual adjusts an environment to create an environmental state optimal for the individual. However, this paradigm fails to respond adequately to changing conditions of the environment and of the individual. The failure of this paradigm is especially evident in environments in which conditions change quickly or the individual is not actively aware of the change of conditions. Some embodiments discussed herein adhere to a new paradigm in which the environment dynamically adapts to the individual, thus improving the biological state of the individual. An example embodiment includes a method of dynamically adapting an environment. The method may include continuously collecting sensor data from multiple biological sensors and multiple environmental sensors. Based on the sensor data, the method includes determining whether an optimal environmental state exists in an environment. The optimal environmental state may be defined in a health and wellness policy and may be configured to promote an optimal biological state of an individual in the environment. In response to the optimal environmental state not existing in the environment, the method may include identifying an environmental condition that differs from the optimal environmental state. A command may be generated that is configured to alter an operational state of an environmental device that affects the environmental condition. Some example embodiments are described herein with reference to the accompanying drawings.

Figure 1:
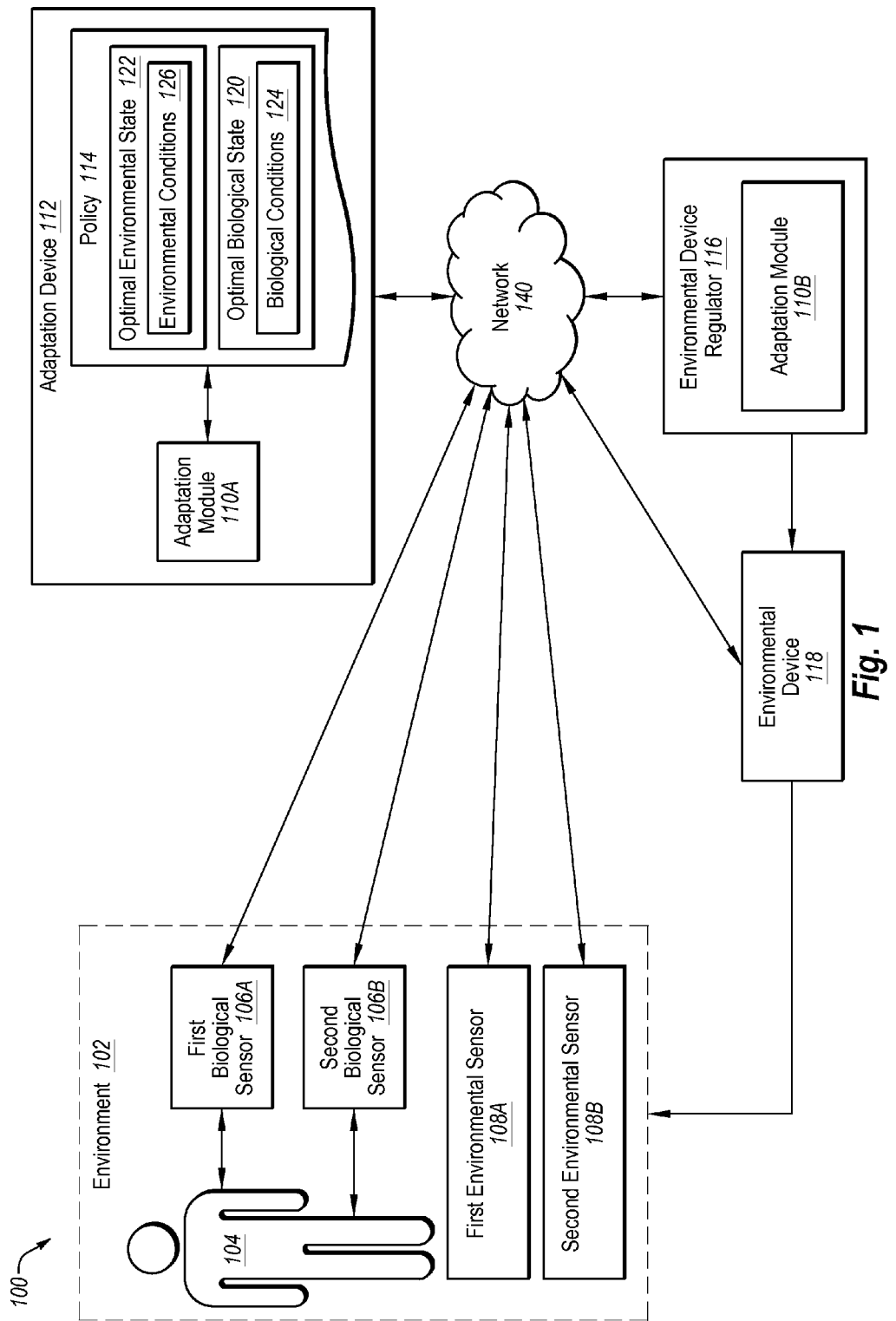
FIG. 1 illustrates an example environmental adaptation system.

FIG. 1 illustrates an example environmental adaptation system (adaptation system) 100, arranged in accordance with at least one embodiment described herein. The adaptation system 100 may be configured to enable adaptation of an environment 102 to promote health and wellness of an individual 104 positioned or otherwise engaged in the environment 102. In some embodiments, the health and wellness of the individual 104 may include an optimal biological state 120 for the individual 104 while performing an activity in the environment 102. The optimal biological state 120 may include one or more biological conditions 124 within optimal ranges and/or in optimal combinations. For example, the biological conditions 124 may include, but are not limited to, a state of mental alertness, a physical position, a physical position of a body part, a level of stress, a heart rate, a blood pressure, a breathing rate, a perspiration level, a body temperature level, and the like.

When the environment 102 is optimized for the health and wellness of the individual 104, the optimal biological state 120 may exist in the environment 102. The optimal biological state 120 may include multiple environmental conditions 126 within optimal ranges and/or in optimal combinations. The environmental conditions 126 may include, but are not limited to, an ambient condition such as temperature, humidity, barometric pressure, fluid motion, sound level, lighting level, a position or operating condition of a piece of equipment in the environment 102, and the like. The optimal biological state 120 and/or the optimal environmental state 122 (collectively, optimal states 120/122) may be defined in a health and wellness policy (policy) 114. For example, one or more of the biological conditions 124, the environmental conditions 126, optimal ranges thereof, and optimal combinations thereof may be defined in the policy 114.

In the adaptation system 100, biological sensors 106A and 106B (generally, biological sensor 106 or biological sensors 106) may be configured to measure one or more biological conditions of the individual 104. In some instances, a single biological sensor 106 may measure multiple biological conditions of the individual 104. Additionally, environmental sensors 108A and 108B (generally, environmental sensor 108 or environmental sensors 108) may be configured to measure one or more environmental conditions of the environment 102. In some instances, a single environmental sensor 108 may measure multiple environmental conditions of the individual 104. To determine whether the optimal states 120/122 exist in the environment 102, the sensor data collected from the biological sensors 106 and the environmental sensors 108 may be compared to the optimal states 120/122 defined in the policy 114. The collection of the sensor data and comparison to the optimal states 120/122 may occur continuously and the environment 102 may be adapted based on the continuously collected sensor data. Accordingly, the environment 102 may dynamically adapt to the individual 104.

As depicted in FIG. 1, the adaptation system 100 may include the environmental sensors 108, the biological sensors 106, an adaptation device 112, an environmental device regulator (regulator) 116, and a network 140. In the adaptation system 100, the environmental sensors 108, the biological sensors 106, the adaptation device 112, and the regulator 116 may communicate via the network 140. Additionally, in the adaptation system 100, adaptation modules 110A-110B (generally, adaptation module 110 or adaptation modules 110) may be included in the regulator 116 and/or the adaptation device 112. The adaptation modules 110 may be configured to determine whether to adapt the environment 102 and/or how to adapt or enable adaptation of the environment 102 based on sensor data from the environmental sensors 108 and/or the biological sensors 106. Additionally, the adaptation modules 110 may be configured to enable communication of the sensor data from the biological sensors 106 and the environmental sensors 108 to the adaptation modules 110 via the network 140.

The network 140 may be wired or wireless and may have numerous different configurations including, but not limited to, a star configuration, token ring configuration, or other configurations. Furthermore, the network 140 may include a local area network (LAN), a wide area network (WAN) (e.g., the Internet), and/or other interconnected data paths across which multiple devices may communicate. In some embodiments, the network 140 may be a peer-to-peer network. The network 140 may also be coupled to or include portions of a telecommunications network that may enable communication of data in a variety of different communication protocols.

In some embodiments, the network 140 includes BLUETOOTH® communication networks and/or cellular communications networks for sending and receiving data including via short messaging service (SMS), multimedia messaging service (MMS), hypertext transfer protocol (HTTP), direct data connection, wireless application protocol (WAP), e-mail, etc. In some embodiments, the network 140 may enable communication, at least partially, of commands to an environmental device 118. The commands may be formatted according to a standard-based protocol such as smart energy profile (SEP), Echonet Lite, OpenADR, or another suitable protocol (e.g., wireless fidelity (Wi-Fi), ZigBee, HomePlug Green, etc.).

The individual 104 may include a person to which the environment 102 may be adapted. The individual 104 may be positioned in or otherwise engaged with the environment 102. The environment 102 may be adapted to an average person, which may be defined in the policy 114, and/or may be at least partially adapted specifically to the individual 104. For example, the individual 104 may have one or more specific preferences, circumstances, or conditions, which may be ascertained and factored into the adaptation of the environment 102. For instance, the individual 104 may be inflicted with an illness, which may be ascertained by the adaptation module 110A based on the sensor data from the biological sensors 106 and may be factored into adaptation of the environment 102.

As depicted in FIG. 1, the adaptation system 100 may be configured to adapt the environment 102 to the individual 104. In some embodiments, multiple individuals similar to and/or including the individual 104 may be positioned in or otherwise engaged with the environment 102. In these and other embodiments, the environment 102 may be adapted for one of the individuals, may be adapted based on an average of one or more biological conditions of the individuals, may prioritize a subset of the individuals, or some combination thereof.

For instance, the environment 102 may be a dorm room shared by three individuals. A first individual may be sensitive to temperature, a second individual may be sensitive to humidity, and a third individual may be sensitive to noise. None of the three individuals may be particularly sensitive to light. During a period of time in which the three individuals are sleeping, the environment 102 may be adapted according to the temperature sensitivity of the first individual, the humidity sensitivity of the second individual, and the noise sensitivity of the third individual. Additionally, the environment 102 may be adapted according to an average light sensitivity of the three individuals. Additionally or alternatively, some embodiments may adapt the environment 102 to one or more pieces of equipment, one or more animals, one or more plants, or some combination thereof The environment 102 may include any setting in which the individual 104 may exist and/or perform an activity. Additionally, the environment 102 may include a sub-environment, which may be independently or conditionally adapted. Additionally or alternatively, the environment 102 may be the sub-environment of a larger environment that may be independently or conditionally adapted. For example, a first environment may include an office in which the individual 104 works. A second environment may include a chair in which the individual 104 sits in the office. The office may be adapted for the individual 104 (e.g., temperature, humidity, fluid flow, etc.) and the chair may be adapted for the individual 104 (e.g., tilt, height, etc.). Some examples of the environment 102 may include, but are not limited to, a sleep environment, a residence, an office, an ergonomic environment, a driving environment (e.g., an automobile or a vehicle), a refrigerator, and an ergonomic environment.

The biological sensors 106 may include and/or may be communicatively coupled to a device that includes a memory, a processor, and network communication capabilities. Each of the biological sensors 106 may include any device configured to measure one or more biological conditions of the individual 104 or to measure a state of the individual 104 or an object that may be indicative of one or more biological conditions of the individual 104. The biological sensors 106 may perform a measurement and may communicate a signal indicative of the measurement to the adaptation module 110A of the adaptation device 112 via the network 140. Additionally or alternatively, the biological sensors 106 may perform a measurement and may determine a biological condition of the individual 104. The biological sensors 106 may then communicate a signal indicative of the biological condition to the adaptation module 110A.

The biological sensors 106 may be associated with the individual 104 such that the biological sensors 106 may make measurements of the individual 104. The biological sensors 106 may be mounted to and/or carried by the individual 104. For instance, the biological sensors 106 may be included in a bracelet, an adhesive electrode, an ear clip, a finger clip, an armband, a necklace, a pocket-sized (or smaller) sensor, or other sensor that the individual 104 wears and/or carries. Additionally or alternatively, the biological sensors 106 may be mounted to an object that is associated with the individual 104. For example, the biological sensors 106 may be affixed to a chair in which the individual 104 sits or may be positioned in a vehicle the individual 104 operates. Additionally or alternatively, the biological sensors 106 may observe an activity of the individual 104. For example, the biological sensors 106 may include cameras that observe eye movement of the individual 104. Some examples of the biological sensors 106 may include, but are not limited to, cameras, accelerometers, on-body temperature sensors, sleep activity sensors, galvanic skin response sensors, electroencephalography (EEG) sensors, blood pressure cuffs, heart rate monitors, electrocardiography (ECG) sensors, percentage of closure of the eyelid (PERCLOS) cameras, electromyography (EMG) sensors, blood glucose sensors, or other biosensors.

The environmental sensors 108 may include and/or may be communicatively coupled to a device that includes a memory, a processor, and network communication capabilities. Each of the environmental sensors 108 may include any device configured to measure one or more environmental conditions of the environment 102 or to measure a state of the environment 102 or an object that may be indicative of one or more environmental conditions of the environment 102. The environmental sensors 108 may perform a measurement and may communicate a signal indicative of the measurement to the adaptation module 110A via the network 140. Additionally or alternatively, the environmental sensors 108 may perform a measurement and may determine an environmental condition of the environment 102. The environmental sensors 108 may then communicate a signal indicative of the environmental condition to the adaptation module 110A.

The environmental sensors 108 may be associated with the environment 102 such that the environmental sensors 108 may make measurements of the environment 102. The environmental sensors 108 may be mounted in the environment 102. For example, the environmental sensors 108 may be introduced into and/or affixed to the environment 102. Additionally or alternatively, the environmental sensors 108 may include and/or may be coupled to a subsystem of the environment 102. For example, the environmental sensors 108 may include a steering subsystem of a vehicle. Additionally or alternatively, the environmental sensors 108 may receive information pertaining to the environment 102. For example, the environmental sensors 108 may access traffic information pertaining to a vehicle. Additionally or alternatively, the environmental sensors 108 may observe an activity occurring in the environment 102. For example, the environment 102 may include a refrigerator associated with the individual 104. The environmental sensors 108 may include positional sensors affixed to foodstuffs that indicate whether the foodstuffs are present in the environment 102. Some examples of the environmental sensors 108 may include, but are not limited to, cameras, accelerometers, thermometers, humidity sensors, light sensors, barometric sensors, air quality sensors, noise sensors, and positional sensors affixed to objects.

The environmental sensors 108 and/or the biological sensors 106 may perform measurements continuously, periodically, randomly, pseudo-randomly, or on-demand. Additionally, the environmental sensors 108 and/or the biological sensors 106 may communicate signals to the adaptation module 110A continuously, periodically, randomly, pseudo-randomly, or on-demand. Accordingly, the adaptation module 110A may have real-time or substantially real-time sensor data pertaining to the individual 104 and the environment 102. As used herein the term "substantially real time" means without a material delay. Thus, the environment 102 may be dynamically adapted continuously, periodically, randomly, pseudo-randomly, or on-demand.

One or more environmental conditions of the environment 102 may be affected through operation of the environmental device 118. Thus, operation of the environmental device 118 may enable adaptation of the environment 102. The environmental device 118 may be positioned in or near the environment 102 or may be related to the environment 102 to affect one or more environmental conditions therein. Some examples of the environmental device 118 may include, but are not limited to, an HVAC component, a filtering mechanism, a humidifier, a light, a speaker, an actuator that controls a position of an object, an alarm, and a subsystem of a vehicle.

In some embodiments, the environmental device 118 may include and/or may be communicatively coupled to a device that includes a memory, a processor, and network communication capabilities. Accordingly, in these and other embodiments, the environmental device 118 may communicate information such as operational state, acknowledgement of received commands, and the like to the adaptation module 110A and/or the adaptation module 110B. Additionally, in embodiments including network communication capabilities, the environmental device 118 may communicate the information via the network 140.

The operation of the environmental device 118 may be controlled by the regulator 116. The regulator 116 may include any device that may affect and/or control operation of the environmental device 118. The regulator 116 may include and/or may be communicatively coupled to a device that includes a memory, a processor, and network communication capabilities. The regulator 116 may include the adaptation module 110B. The adaptation module 110B may be configured to receive commands from the adaptation module 110A via the network 140. The adaptation module 110B may then communicate the commands to the environmental device 118. In the depicted adaptation system 100, the communication of the command may or may not be via the network 140. Some examples of the regulator 116 may include a thermostat, a switch coupled to an actuator, a dimmer switch, and a humidifier setting switch.

In some embodiments, the regulator 116 and the environmental device 118 may be included in a single component. For example, the adaptation module 110B that receives a command from the adaptation module 110A may be incorporated in the environmental device 118. The environmental device 118 may implement the command locally rather than perform an additional communication. Additionally or alternatively, the regulator 116 and/or the environmental device 118 may be located in the environment 102.

The adaptation device 112 may include any device or server configured to collect sensor data from the biological sensors 106 and the environmental sensors 108, process the sensor data, and generate a command configured to alter an operational state of the environmental device 118 based on the processed sensor data. In some embodiments, the adaptation device 112 may include a computing device that includes a processor, a memory, and network communication capabilities. Some specific examples of the adaptation device 112 may include a hardware server, a laptop computer, a desktop computer, a tablet computer, a mobile telephone, a smartphone, a personal digital assistant (PDA), a mobile e-mail device, a portable game player, a portable music player, a television with one or more processors embedded therein or coupled thereto, or other electronic device capable of processing data and accessing and communicating via the network 140.

In some embodiments, the adaptation device 112 may include the adaptation module 110A. The adaptation module 110A may be configured to collect the sensor data from the biological sensors 106 and the environmental sensors 108 via the network 140. In some embodiments, the sensor data may be transmitted by the biological sensors 106 and/or the environmental sensors 108. Additionally or alternatively, the adaptation module 110A may harvest the sensor data from the biological sensors 106 and/or the environmental sensors 108 via the network 140.

The sensor data may be collected in data streams in some embodiments. For instance, the sensor data may be continuously collected. Thus, the sensor data may be formatted in one or more streams of data. Alternately or additionally, the sensor data may be batch transferred, which may include the sensor data formatted in batches, for instance.

The adaptation module 110A may then process the sensor data. For example, the adaptation module 110A may remove noise from the sensor data. Additionally or alternatively, the adaptation module 110A may combine the sensor data. Based on the combined sensor data, the adaptation module 110A may compute an actual environmental state of the environment 102 and/or an actual biological state of the individual 104.

The adaptation module 110A may then determine whether the optimal environmental state 122 exists in the environment 102 and/or whether an optimal biological state 120 of the individual 104 exists. The optimal states 120/122 may be defined in the policy 114.

The optimal states 120/122 may be based on the type of the environment 102, the individual 104, an expected type of individual in the environment, a specific condition of the individual 104, other factors, or any combination thereof. Additionally or alternatively, the optimal biological state 120 may be based on the actual biological state computed by the adaptation module 110A. Likewise, the optimal biological state 120 may be based on the actual environmental state computed by the adaptation module 110A. For example, the policy 114 may include multiple optimal environmental states that pertain to the environment 102 and may vary the optimal environmental states based on the actual biological state of the individual 104 and/or an activity being performed in the environment 102. The policy 114 may further define an optimal biological state 120 that corresponds to the computed actual biological state of the individual 104.

The policy 114 may be downloaded or otherwise accessed from a third party. The policy 114 may be statically defined or may change or learn dynamically as the individual 104 interacts in the environment 102. In some embodiments, the policy 114 may be updatable. For instance, as biological conditions are determined to be important in the environment 102, the policy 114 may be updated to reflect the determination. Additionally or alternatively, the policy 114 may be configured to interact with the biological sensor 106 and/or the environmental sensor 108 and then later updated to interact with other biological sensors and/or other environmental sensors.

The optimal states 120/122 may include sets of limits for the environmental conditions 126 and/or the biological conditions 124. The limits may be configured to promote an optimal biological state 120 of the individual 104 or may be configured as an optimal biological state 120 of the individual 104. The limits may include one or more of weighted thresholds, Boolean combinations of limits, optimal ranges including minimum and/or maximum thresholds for the environmental conditions 126, and/or biological conditions 124.

Based on the sensor data, the adaptation module 110A may identify an environmental condition that differs from the optimal biological state 120. The adaptation module 110A may then identify a biological condition of the individual 104 that deviates from a limit of a biological condition 124 of an optimal biological state 120 and that is influenced by the identified environmental condition.

The adaptation module 110A may then generate a command. The command may be configured to alter an operational state of the environmental device 118 that affects the environmental condition. The command may be communicated to the regulator 116, which may then communicate the command to the environmental device 118. The adaptation module 110A may collect updated sensor data from the biological sensors 106 and the environmental sensors 108. The adaptation module 110A may then determine whether the command has placed or will place the environment 102 in the optimal biological state 120. In response to the command not placing the environment 102 in the optimal biological state 120, the adaptation module 110A may identify an updated environmental condition that differs from the optimal biological state 120 and may generate an updated command configured to alter an operational state of the environmental device 118 or another environmental device (not shown) that affects the updated environmental condition.

Modifications, additions, or omissions may be made to the adaptation system 100 without departing from the scope of the present disclosure. Specifically, in embodiments depicted in FIG. 1 the adaptation system 100 may adapt one environment 102 to one individual 104, based on sensor data from two biological sensors 106 and two environmental sensors 108. The sensor data may be received by one environmental device 118, and commands may be communicated to one regulator 116 to affect operation of one adaptation device 112. However, the present disclosure applies to an adaptation system architecture that adapts one or more environments to one or more individuals based on sensor data one or more biological sensors (e.g., one biological sensor measuring multiple biological conditions) and one or more environmental sensors (e.g., one environmental sensor measuring multiple environmental conditions). The sensor data may be received by one or more adaptation devices that may communicate commands to one or more regulators to affect operation of one or more environmental devices.

Moreover, the separation of various components in the embodiments described herein is not meant to indicate that the separation occurs or exists in all embodiments. Moreover, it may be understood with the benefit of this disclosure that the described components and servers may be integrated together in a single component or server or implemented separately as multiple components or servers.

The adaptation modules 110 may include code and routines for adaptation of the environment 102. In some embodiments, the adaptation modules 110 act in part as a thin-client application that may be stored on the adaptation device 112 and in part as components that may be stored on the regulator 116 of the adaptation system 100. In some embodiments, the adaptation modules 110 may be implemented using hardware including a field-programmable gate array (FPGA) or an application-specific integrated circuit (ASIC). In some other instances, the adaptation modules 110 may be implemented using a combination of hardware and software. In some embodiments, the adaptation modules 110 may be stored in a combination of the adaptation device 112 and the regulator 116.

In the adaptation system 100, memory (e.g., memory included in one or more of the biological sensors 106, the environmental sensors 108, the environmental device 118, the regulator 116, and the adaptation device 112) may include a non-transitory memory that stores data for providing the functionality described herein. The memory may be included in storage that may be a dynamic random access memory (DRAM) device, a static random access memory (SRAM) device, flash memory, or some other memory devices. In some embodiments, the storage also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

Figure 2:
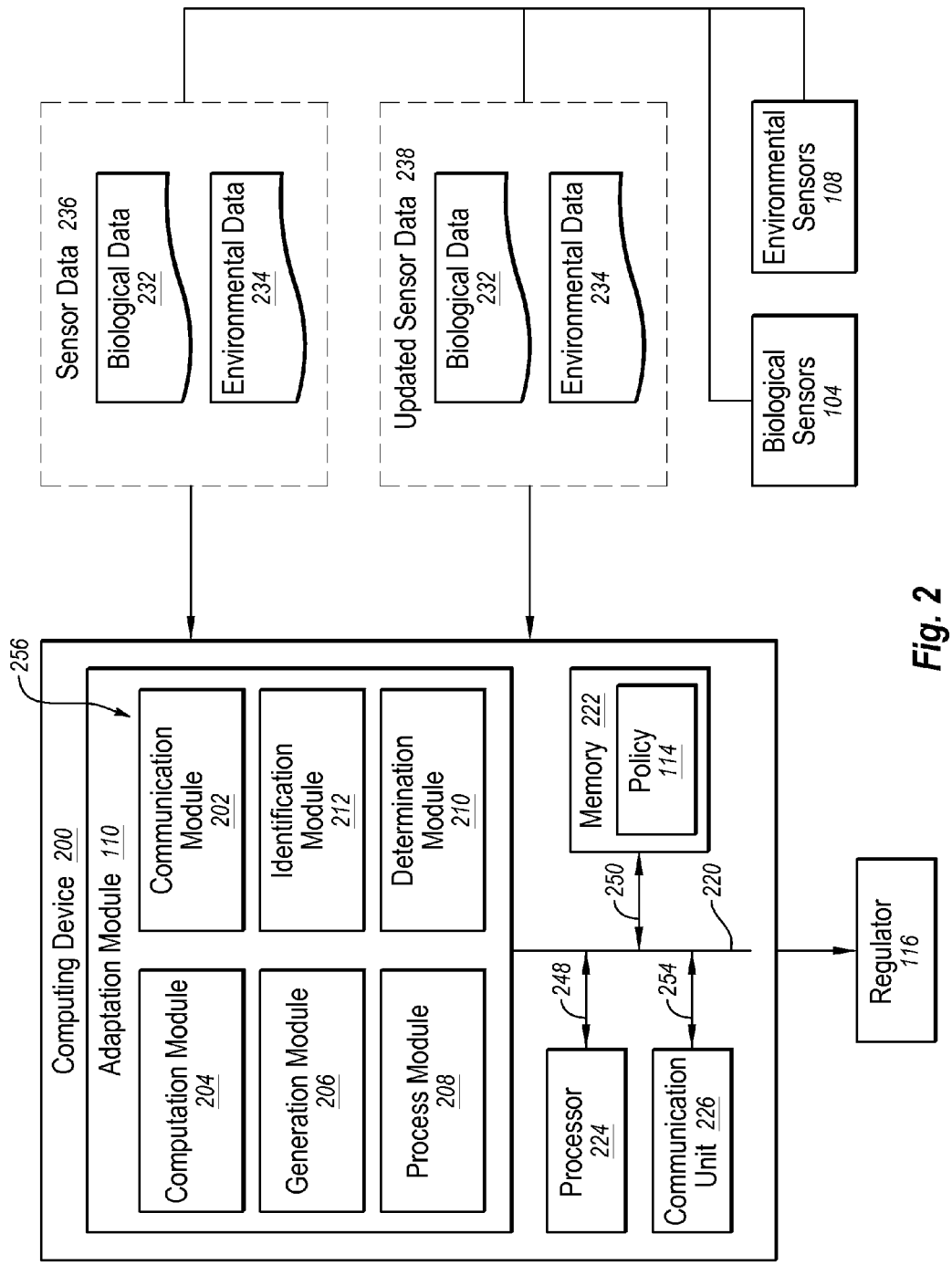
FIG. 2 illustrates an example computing device that may be implemented in the environmental adaptation system of FIG. 1.

Referring now to FIG. 2, an example of the adaptation module 110 is shown in more detail. FIG. 2 is a block diagram of a computing device 200 that includes the adaptation module 110, a processor 224, a memory 222, and a communication unit 226. The components of the computing device 200 may be communicatively coupled by a bus 220. In some embodiments, the computing device 200 may include the adaptation device 112 and/or the regulator 116 of the adaptation system 100 of FIG. 1.

With combined reference to FIGS. 1 and 2, the processor 224 may include an arithmetic logic unit (ALU), a microprocessor, a general-purpose controller, or some other processor array to perform computations and environment adaptation. The processor 224 may be coupled to the bus 220 via a signal line 248 for communication with the other components (e.g., 110, 226, and 222). The processor 224 generally processes data signals and may include various computing architectures including a complex instruction set computer (CISC) architecture, a reduced instruction set computer (RISC) architecture, or an architecture implementing a combination of instruction sets. Although FIG. 2 includes a single processor 224, multiple processors may be included in the computing device 200. Other processors, operating systems, and physical configurations may be possible.

The memory 222 may be configured to store instructions and/or data that may be executed by the processor 224. The memory 222 may be coupled to the bus 220 via a signal line 250 for communication with the other components. The instructions and/or data may include code for performing the techniques or methods described herein. The memory 222 may be a DRAM device, an SRAM device, flash memory, or some other memory device. In some embodiments, the memory 222 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

In the depicted embodiment, the memory 222 includes the policy 114. The policy 114 may define optimal states 120/122. The policy 114 may be configured to enable access to the optimal states 120/122 during the adaptation of the environment 102. The policy 114 is depicted as part of the memory 222 of the computing device 200. In some embodiments, the policy 114 or some portion of the policy 114 may be stored remotely and accessed remotely via the network 140.

The communication unit 226 may be configured to transmit and receive data to and from at least one of the biological sensors 106, the environmental sensors 108, the environmental device 118, the regulator 116, and the adaptation device 112 depending upon where the adaptation module 110 is stored. The communication unit 226 may be coupled to the bus 220 via a signal line 254. In some embodiments, the communication unit 226 includes a port for direct physical connection to the network 140 or to another communication channel. For example, the communication unit 226 may include a USB, SD, CAT-5, or similar port for wired communication with the components of the adaptation system 100. In some embodiments, the communication unit 226 includes a wireless transceiver for exchanging data via communication channels using one or more wireless communication methods, including IEEE 802.11, IEEE 802.16, BLUETOOTH®, or another suitable wireless communication method.

In some embodiments, the communication unit 226 includes a cellular communications transceiver for sending and receiving data over a cellular communications network including via SMS, MMS, HTTP, direct data connection, WAP, e-mail, or another suitable type of electronic communication. In some embodiments, the communication unit 226 includes a wired port and a wireless transceiver. The communication unit 226 may also provide other conventional connections to the network 140 for distribution of files and/or media objects using standard network protocols including transmission control protocol/internet protocol (TCP/IP), HTTP, HTTP secure (HTTPS), and simple mail transfer protocol (SMTP), etc.

In the embodiment of FIG. 2, the adaptation module 110 may include a communication module 202, a computation module 204, a generation module 206, a process module 208, a determination module 210, and an identification module 212, which are collectively referred to in FIG. 2 as modules 256. One or more of the modules 256 may be implemented as software including one or more routines configured to perform one or more operations. The modules 256 may include a set of instructions executable by the processor 224 to provide the functionality described below. In some instances, the modules 256 may be stored in or at least temporarily loaded into the memory 222 of the computing device 200 and may be accessible and executable by the processor 224. One or more of the modules 256 may be adapted for cooperation and communication with the processor 224 and components of the computing device 200 via the bus 220.

The communication module 202 may be configured to handle communications between the adaptation module 110 and other components of the computing device 200 (e.g., 224, 222, and 226). The communication module 202 may be configured to send and receive data, via the communication unit 226, to and from one or more of the biological sensors 106, the environmental sensors 108, the environmental device 118, the regulator 116, and the adaptation device 112. In some instances, the communication module 202 may cooperate with the other modules (e.g., 204, 206, 208, 210, and 212) to receive and/or forward, via the communication unit 226, data from the components of the adaptation system 100.

In some embodiments, the communication module 202 may be configured to collect sensor data 236. The sensor data 236 may include biological data 232 collected from the biological sensors 106 and environmental data 234 collected from the environmental sensors 108. The sensor data 236 may be collected via the network 140 and the communication unit 226. The communication module 202 may communicate the sensor data 236 to the process module 208.

The process module 208 may be configured to process the sensor data 236. In some embodiments, the process module 208 receives the sensor data 236 and removes noise from the sensor data 236. For example, the noise may be due to distortion of a value or an addition of spurious values. One or more techniques from signal processing algorithms or image processing algorithms such as smoothing algorithms or filters may be used to reduce the noise. The noise with deterministic patterns or artifacts may be identified and handle appropriately.

The signal processing algorithms may be different based on the specific type of the environmental sensors 108 and/or the specific type of the biological sensors 106. For example, an ECG may have specific noise removal techniques that may include adaptive recurrent filtering, low-pass filtering with a cut-off frequency, adaptive filtering, notch filtering, or any combination thereof. In some embodiments, the environmental sensors 108 and/or the biological sensors 106 may process or partially process the sensor data 236 prior to communication to the computing device 200.

Additionally, in some embodiments, the quality of the data may be compromised with missing values during the measurements. One or more techniques may be implemented to detect missing values and correct them. For example, the process module 208 may interpolate the sensor data 236 to estimate a missing value.

Additionally or alternatively, the process module 208 may combine the sensor data 236. For example, the sensor data 236 may be received from multiple sensors. The sensor data 236 may be combined in a central hub and/or time synchronized. The process module 208 may communicate the combined sensor data 236 to the computation module 204. In some embodiments, the sensor data 236 may be combined at least partially as described in U.S. patent application Ser. No. 13/107,697, which was filed May 13, 2011 and is incorporated herein by reference in its entirety.

The computation module 204 may be configured to compute an actual environmental state of the environment 102 and an actual biological state of the individual 104 (collectively, actual states) based on the combined sensor data. The actual states may include, for example, an activity of the individual 104 (e.g., the individual 104 is driving), a state of the individual 104 (e.g., the individual 104 is tired or sick), an activity of the environment 102 (e.g., the environment 102, which is a vehicle, is driving), or a state of the environment 102 (e.g., the environment 102, which is an office, is open or closed). The actual states may be computed from the sensor data 236. A signal indicating the actual states may be communicated to the determination module 210.

The determination module 210 may be configured to determine whether the optimal states 120/122 exist in the environment 102. The optimal states 120/122 may be defined according to the policy 114. The determination module 210 may communicate a signal indicating whether the optimal states 120/122 exist to the identification module 212.

The identification module 212 may be configured to identify conditions that differ from the optimal states 120/122. For example, in response to the optimal states 120/122 not existing in the environment 102, the identification module 212 may identify an environmental condition that differs from the optimal biological state 120. Additionally, the identification module 212 may identify a biological condition that deviates from a limit of a biological condition 124 defined in the optimal biological state 120 and is influenced by the environmental condition. The identification module 212 may communicate the environmental condition and/or the biological condition to the generation module 206.

The generation module 206 may generate a command. The command may be configured to alter an operational state of the environmental device 118 that affects the environmental condition. The generation module 206 may communicate the command to the communication module 202 that may communicate the command to the regulator 116 via the network 140 and/or the communication unit 226.

The communication module 202 may then collect updated sensor data 238. The updated sensor data 238 may include the biological data 232 and the environmental data 234. The determination module 210 may determine whether the command placed the environment 102 in the optimal biological state 120. In response to the command not having placed the environment in the optimal biological state 120, the identification module 212 may identify an updated environmental condition that differs from the optimal biological state 120. Additionally, the generation module 206 may generate an updated command configured to alter a second operational state of the environmental device 118 or another environmental device that affects the updated environmental condition.

Figure 3:
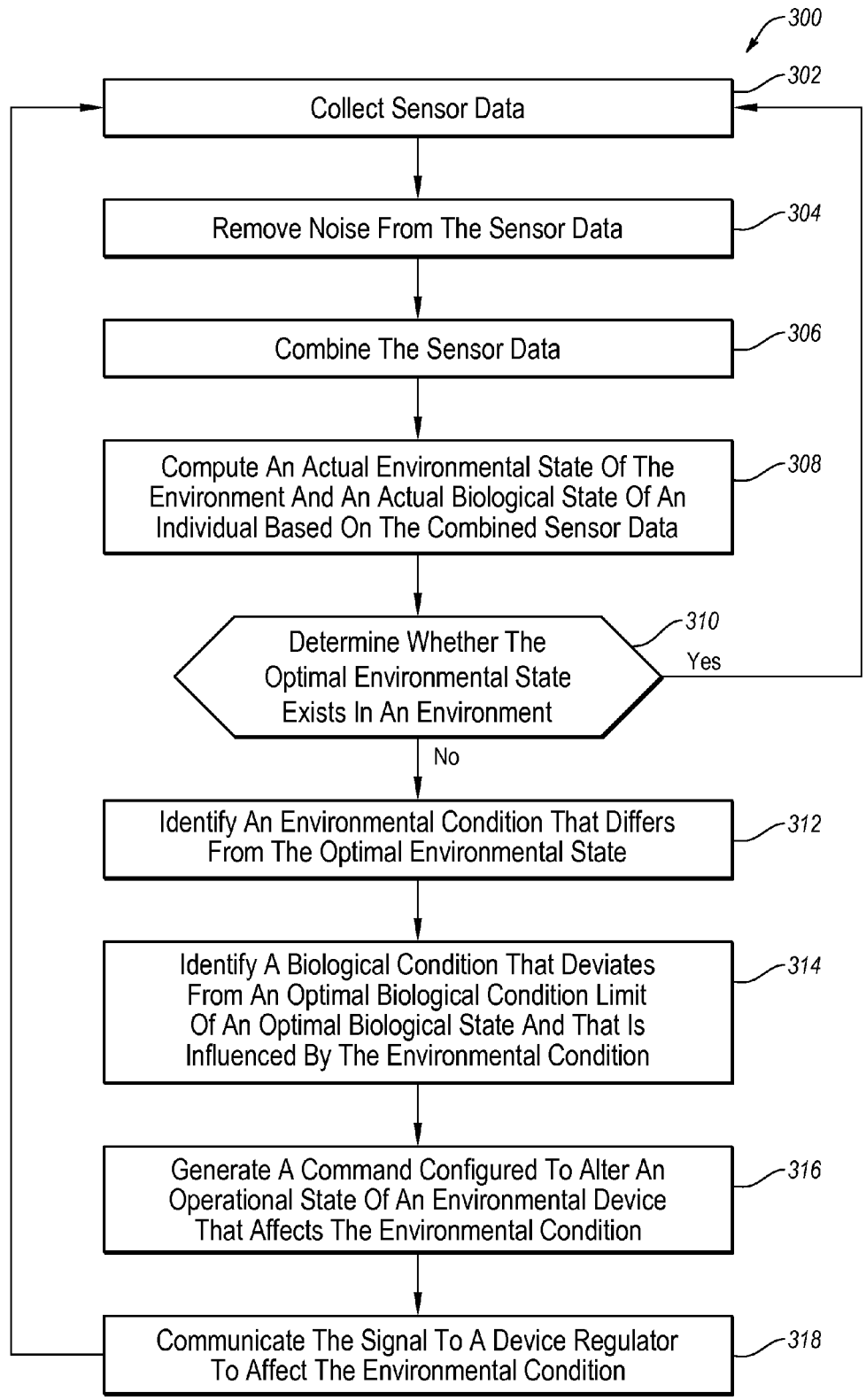
FIG. 3 is a flow diagram of an example method of dynamic environment adaptation.

FIG. 3 is a flow diagram of an example method 300 of adapting an environment, arranged in accordance with at least one embodiment described herein. The method 300 may be performed in an adaptation system such as the adaptation system 100 of FIG. 1 to control an environment. Some example environments that may be adapted according to the method 300 of FIG. 3 may include, but are not limited to, a vehicle environment, an office environment, an ergonomics environment, and a sleep environment.

The method 300 may be programmably performed in some embodiments by the computing device 200 described with reference to FIG. 2. Additionally or alternatively, the method 300 may be programmably performed by the adaptation device 112. The adaptation device 112 and/or the computing device 200 may include or may be communicatively coupled to a non-transitory computer-readable medium (e.g., the memory 222 of FIG. 2) having stored thereon or encoded therein programming code or instructions that are executable by a processor to perform or cause performance of the method 300. Additionally or alternatively, the adaptation device 112 and/or the computing device 200 may include a processor (e.g., the processor 224 of FIG. 2) that is configured to execute computer instructions to cause or control performance of the method 300. Although illustrated as discrete blocks, various blocks may be divided into additional blocks, combined into fewer blocks, or eliminated, depending on the desired implementation.

At block 302, sensor data may be collected. The sensor data may be collected from one or more biological sensors and/or one or more environmental sensors. For example, with reference to FIG. 1, the adaptation module 110A may collect the sensor data from the biological sensors 106 and the environmental sensors 108.

At block 304, noise may be removed from the sensor data. At block 306, the sensor data may be combined. For example, with reference to FIG. 1, the sensor data may be collected by the adaptation module 110A. The adaptation module 110A may remove the noise from the sensor data and may combine the sensor data.

At block 308, an actual environmental state of the environment and an actual biological state of an individual may be computed. The actual environmental state and the actual biological state may be based on the combined sensor data. For example, with reference to FIG. 1, the adaptation module 110A may compute the actual environmental state of the environment 102 and the actual biological state of the individual 104 based on sensor data collected from the biological sensors 106 and the environmental sensors 108.

At block 310, it may be determined whether the optimal environmental state exists in the environment. The optimal environmental state may be defined in a policy. The optimal environmental state may include limits for one or more environmental conditions configured to promote an optimal biological state of the individual while performing an activity in the environment. The limits may include one or more of weighted thresholds, Boolean combinations of the limits, and optimal ranges such minimum and/or maximum thresholds for one or more environmental conditions. For example, with reference to FIG. 1, the adaptation module 110A may determine whether the optimal biological state 120 exists in the environment 102 by comparing measured environmental conditions to the environmental conditions 126 included in the optimal biological state 120 defined in the policy 114.

In response to the optimal environmental state existing ("Yes" at block 310), the method 300 may proceed to block 302. In response to the optimal environment state not existing ("No" at block 310), the method 300 may proceed to block 312.

At block 312, an environmental condition that differs from the optimal environmental state may be identified. At block 314, a biological condition may be identified. The biological condition may exceed a limit of an optimal biological condition of an optimal biological state and may be influenced by the environmental condition. The optimal biological state may be defined by the policy. For example, with reference to FIG. 1, the adaptation module 110A may identify the environmental condition that differs from the optimal environmental state 122 of the environment 102 and the biological condition that differs from the optimal biological state 120 of the individual 104.

At block 316, a command may be generated. The command may be configured to alter an operational state of an environmental device that affects the environmental condition. For example, with reference to FIG. 1, the adaptation module 110A may generate a command configured to alter an operational state of the environmental device 118.

At block 318, the command may be communicated to a regulator to affect the environmental condition. For example, with reference to FIG. 1, the adaptation module 110A may communicate the command to the regulator 116 via the network 140. The method 300 may continue to block 302 in which updated sensor data may be collected. One or more of the operations or steps discussed with reference to blocks 304, 306, 308, 310, 312, 314, 316, and 318 may be repeated using the updated sensor data.

One skilled in the art will appreciate that, for this and other procedures and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the disclosed embodiments.

Figure 4:
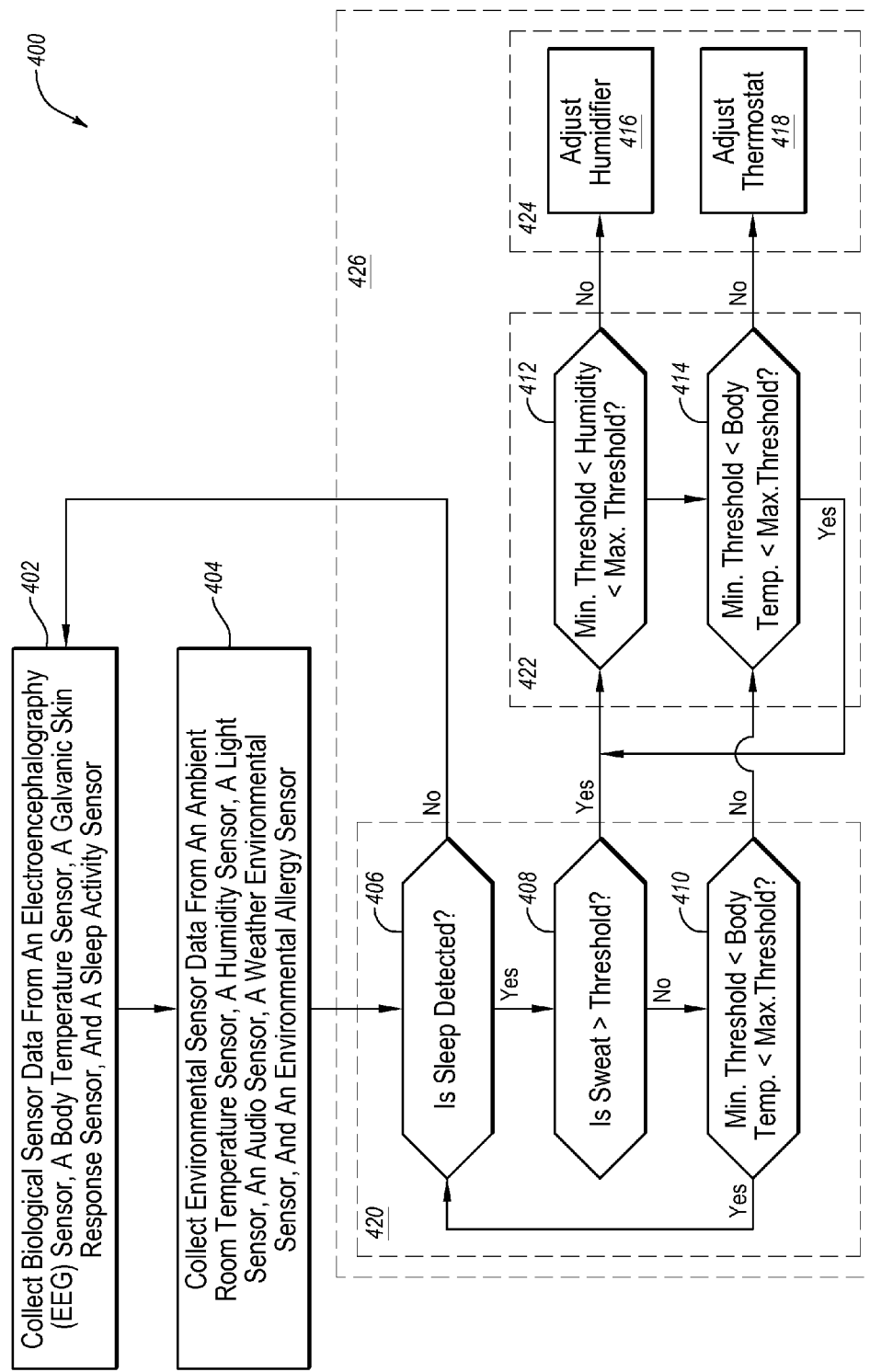
FIG. 4 is a flow diagram of an example method of sleep environment adaptation.

FIG. 4 is a flow diagram of an example method 400 for adapting a sleep environment, arranged in accordance with at least one embodiment described herein. The method 400 may be performed in an adaptation system such as the adaptation system 100 of FIG. 1.

The method 400 may be programmably performed in some embodiments by the computing device 200 described with reference to FIG. 2. Additionally or alternatively, the method 400 may be programmably performed by the adaptation device 112. The adaptation device 112 and/or the computing device 200 may include or may be communicatively coupled to a non-transitory computer-readable medium (e.g., the memory 222 of FIG. 2) having stored thereon or encoded therein programming code or instructions that are executable by a processor to perform or cause performance of the method 400. Additionally or alternatively, the adaptation device 112 and/or the computing device 200 may include a processor (e.g., the processor 224 of FIG. 2) that is configured to execute computer instructions to cause or control performance of the method 400. Although illustrated as discrete blocks, various blocks may be divided into additional blocks, combined into fewer blocks, or eliminated, depending on the desired implementation.

At block 402, biological sensor data may be collected. In some embodiments, the biological sensor data may be collected from one or more of an EEG sensor, a body temperature sensor, a galvanic skin response sensor, and a sleep activity sensor.

At block 404, environmental sensor data may be collected. In some embodiments, the environmental sensor data may be collected from one or more of an ambient room temperature sensor, a humidity sensor, a light sensor, an audio sensor, a weather environmental sensor, and an environmental allergy sensor.

At block 406, it may be determined whether sleep is detected. In response to sleep not being detected, ("No" at 406), the method 400 may proceed to block 402 and may repeat one or more of blocks 402, 404, and 406 until sleep is detected. In response to sleep being detected, ("Yes" at 406), the method 400 may proceed to block 408. At block

408, it may be determined whether a measured sweat level is above a threshold ("Is Sweat>Threshold?"). In response to the measured sweat level being above the threshold ("Yes" at 408), the method 400 may proceed to block 412. At block 412, it may be determined whether a measured humidity level is between a minimum threshold and a maximum threshold ("Min. Threshold<Humidity<Max. Threshold?"). In response to the measured humidity level not being between the minimum threshold and the maximum threshold ("No" at 412), the method 400 may proceed to block 416. At block 416, a command may be generated to adjust a humidifier ("Adjust Humidifier").

In response to the measured sweat level being below the threshold ("No" at 408), the method 400 may proceed to block 410. At block 410, it may be determined whether a measured body temperature is between a minimum threshold and a maximum threshold ("Min. Threshold<Body Temp.<Max.Threshold?").

In response to the measured body temperature not being between the minimum threshold and the maximum threshold ("No" at 410), the method 400 may proceed to block 414. At block 414, it may be determined whether a measured room temperature is between a minimum threshold and a maximum threshold ("Min. Threshold<Room Temp.<Max. Threshold?"). In response to the measure room temperature not being between the minimum threshold and the maximum threshold ("No" at 414), the method 400 may proceed to block 418. At block 418, a command to adjust a thermostat ("Adjust Thermostat") may be generated.

In response to the measure body temperature being between the minimum threshold and the maximum threshold ("Yes" at 410), the method 400 may proceed to block 406. In response to the measured humidity being between the minimum threshold and the maximum threshold ("Yes" at 412), the method 400 may proceed from block 412 to block 414. Additionally, in response to the measured room temperature being between the minimum threshold and the maximum threshold ("Yes" at 414), the method 400 may proceed from block 414 to block 412.

In FIG. 4, the blocks 406, 408, and 410 may be included in or defined in an optimal biological state 420. Additionally, block 412 and block 414 may be included in or defined in an optimal environmental state 422, and the blocks 416 and 418 may be commands 424. Additionally still, blocks 406, 408, 410, 412, 414, 416, and 418 may be included in or defined in a policy 426. In some embodiments, the optimal biological state 420 may include more blocks that may include more thresholds of other biological conditions. Additionally or alternatively, the optimal environmental state 422 may include more blocks that may include more thresholds of other environmental conditions. Additionally or alternatively, the commands 424 may include more blocks with more commands.

Figure 5:
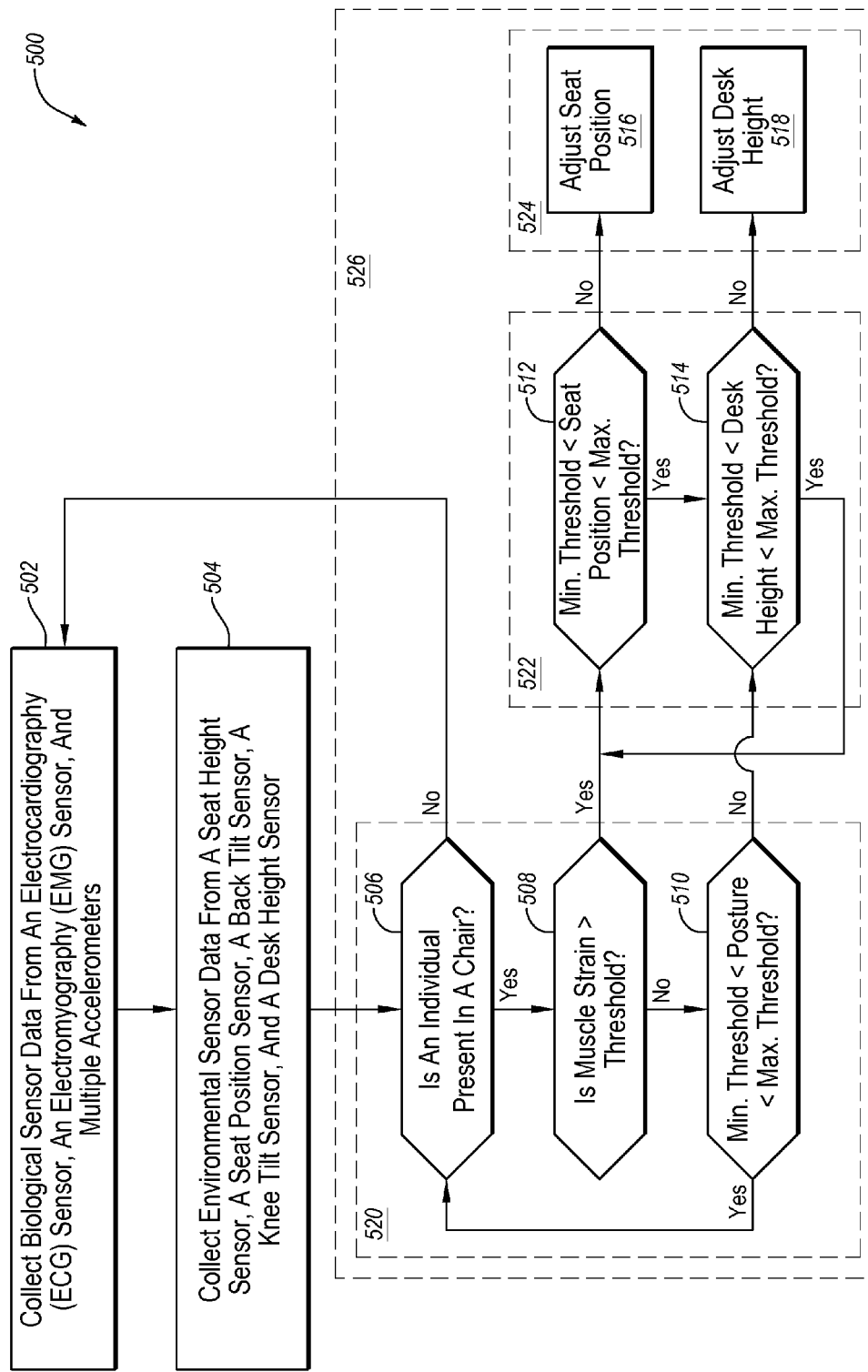
FIG. 5 is a flow diagram of an example method of ergonomic environment adaptation.

FIG. 5 is a flow diagram of an example method 500 for adapting an ergonomic environment, arranged in accordance with at least one embodiment described herein. The method 500 may be performed in an adaptation system such as the adaptation system 100 of FIG. 1.

The method 500 may be programmably performed in some embodiments by the computing device 200 described with reference to FIG. 2. Additionally or alternatively, the method 500 may be programmably performed by the adaptation device 112. The adaptation device 112 and/or the computing device 200 may include or may be communicatively coupled to a non-transitory computer-readable medium (e.g., the memory 222 of FIG. 2) having stored thereon or encoded therein programming code or instructions that are executable by a processor to perform or cause performance of the method 300. Additionally or alternatively, the adaptation device 112 and/or the computing device 200 may include a processor (e.g., the processor 224 of FIG. 2) that is configured to execute computer instructions to cause or control performance of the method 500. Although illustrated as discrete blocks, various blocks may be divided into additional blocks, combined into fewer blocks, or eliminated, depending on the desired implementation.

At block 502, biological sensor data may be collected. In some embodiments, the biological sensor data may be collected from one or more of an ECG sensor, an EMG sensor, and multiple accelerometers.

At block 504, environmental sensor data may be collected. In some embodiments, the environmental sensor data may be collected from one or more of a seat height sensor, a seat position sensor, a back tilt sensor, a knee tilt sensor, and a desk height sensor.

At block 506, it may be determined whether an individual is present in a chair. In response to the individual not being present in the chair, ("No" at 506), the method 500 may proceed to block 502 and may repeat one or more of blocks 502, 504, and 506 until the individual is present in the chair. In response to the individual being present in the chair, ("Yes" at 506), the method 500 may proceed to block 508. At block 508, it may be determined whether a measured muscle strain is above a threshold ("Is Muscle Strain>Threshold?"). In response to the measured muscle strain being above the threshold ("Yes" at 508), the method 500 may proceed to block 512. At block 512, it may be determined whether a measured seat position is between a minimum threshold and a maximum threshold ("Min. Threshold<Seat Position<Max. Threshold?"). In response to the measured seat position not being between the minimum threshold and the maximum threshold ("No" at 512), the method 500 may proceed to block 516. At block 516, a command may be generated to adjust a seat position ("Adjust Seat Position"). The command may be communicated to an actuator that adjusts a seat position.

In response to the measured muscle strain being below the threshold ("No" at 508), the method 500 may proceed to block 510. At block 510, it may be determined whether a posture is between a minimum threshold and a maximum threshold ("Min. Threshold<Posture<Max. Threshold?").

In response to the measured posture not being between the minimum threshold and the maximum threshold ("No" at 510), the method 500 may proceed to block 514. At block 514, it may be determined whether a measured desk height is between a minimum threshold and a maximum threshold ("Min. Threshold<Desk Height<Max. Threshold?"). In response to the measured desk height not being between the minimum threshold and the maximum threshold ("No" at 514), the method 500 may proceed to block 518. At block 518, a command to adjust a desk height ("Adjust Desk Height") may be generated. The command may be communicated to an actuator that adjusts a height of a desk.

In response to the measured posture being between the minimum threshold and the maximum threshold ("Yes" at 510), the method 500 may proceed to block 506. In response to the measured seat position being between the minimum threshold and the maximum threshold ("Yes" at 512), the method 500 may proceed from block 512 to block 514. Additionally, in response to the measured desk height being between the minimum threshold and the maximum threshold ("Yes" at 514), the method 500 may proceed from block 514 to block 512.

In FIG. 5, the blocks 506, 508, and 510 may be included in or defined in an optimal biological state 520. Additionally, block 512 and block 514 may be included in or defined in an optimal environmental state 522 and blocks 516 and 518 may be commands 524. Additionally still, blocks 506, 508, 510, 512, 514, 516, and 518 may be included in or defined by a policy 526. In some embodiments, the optimal biological state 520 may include more blocks that may include more thresholds of other biological conditions. Additionally or alternatively, the optimal environmental state 522 may include more blocks that may include more thresholds of other environmental conditions. Additionally or alternatively, the commands 524 may include more blocks with more commands.

Figure 6:
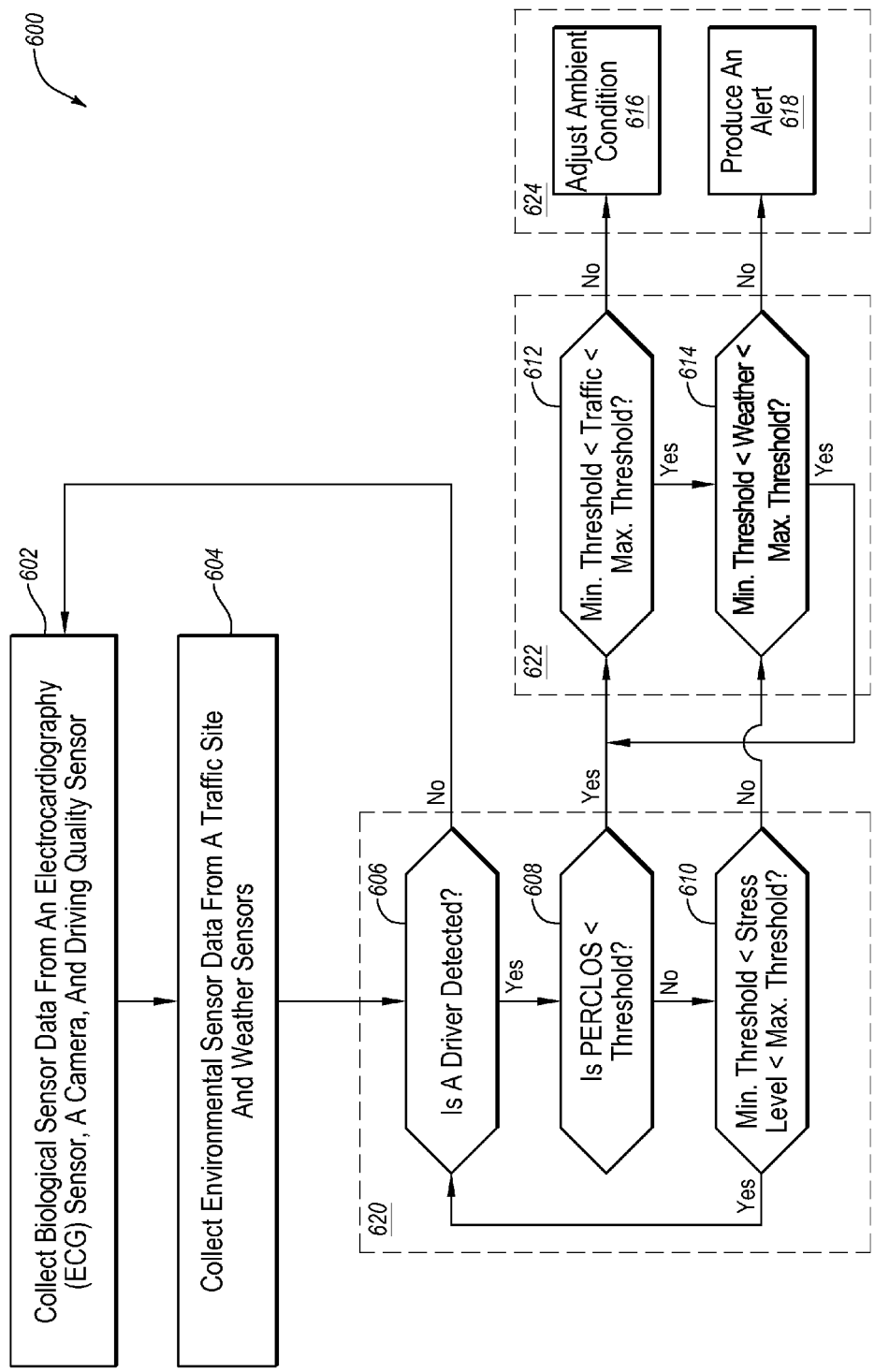
FIG. 6 is a flow diagram of an example method of driving environment adaptation, all arranged in accordance with at least one embodiment described herein.

FIG. 6 is a flow diagram of an example method 600 for adapting a driving environment, arranged in accordance with at least one embodiment described herein. The method 600 may be performed in an adaptation system such as the adaptation system 100 of FIG. 1.

The method 600 may be programmably performed in some embodiments by the computing device 200 described with reference to FIG. 2. Additionally or alternatively, the method 400 may be programmably performed by the adaptation device 112. The adaptation device 112 and/or the computing device 200 may include or may be communicatively coupled to a non-transitory computer-readable medium (e.g., the memory 222 of FIG. 2) having stored thereon or encoded therein programming code or instructions that are executable by a processor to perform or cause performance of the method 600. Additionally or alternatively, the adaptation device 112 and/or the computing device 200 may include a processor (e.g., the processor 224 of FIG. 2) that is configured to execute computer instructions to cause or control performance of the method 600. Although illustrated as discrete blocks, various blocks may be divided into additional blocks, combined into fewer blocks, or eliminated, depending on the desired implementation.

At block 602, biological sensor data may be collected. In some embodiments, the biological sensor data may be collected from one or more of an ECG sensor, a camera, and a driving quality sensor.

At block 604, environmental sensor data may be collected. In some embodiments, the environmental sensor data may be collected from one or more of traffic site and weather sensors.

At block 606, it may be determined whether a driver is detected. In response to the driver not being detected, ("No" at 606), the method 600 may proceed to block 602 and may repeat one or more of blocks 602, 604, and 606 until the driver is detected. In response to the driver being detected, ("Yes" at 606), the method 600 may proceed to block 608. At block 608, it may be determined whether a measured PERCLOS level is below a threshold ("Is PERCLOS<Threshold?"). In response to the PERCLOS level being below the threshold ("Yes" at 608), the method 600 may proceed to block 612. At block 612, it may be determined whether traffic conditions are between a minimum threshold and a maximum threshold ("Min. Threshold<Traffic<Max. Threshold?"). In response to the traffic conditions not being between the minimum threshold and the maximum threshold ("No" at 612), the method 600 may proceed to block 616. At block 416, a command may be generated to adjust an ambient condition of a vehicle ("Adjust Ambient Condition").

In response to the measured PERCLOS level being above the threshold ("No" at 608), the method 600 may proceed to block 610. At block 610, it may be determined whether a measured stress level is between a minimum threshold and a maximum threshold ("Min. Threshold<Stress Level<Max. Threshold?").

In response to the measured stress level not being between the minimum threshold and the maximum threshold ("No" at 610), the method 600 may proceed to block 614. At block 614, it may be determined whether a weather condition is between a minimum threshold and a maximum threshold ("Min. Threshold<Weather<Max. Threshold?"). In response to the weather condition not being between the minimum threshold and the maximum threshold ("No" at 614), the method 600 may proceed to block 618. At block 618, a command to produce an alert ("Produce An Alert") may be generated.

In response to the measure stress level being between the minimum threshold and the maximum threshold ("Yes" at 610), the method 600 may proceed to block 606. In response to the traffic conditions being between the minimum threshold and the maximum threshold ("Yes" at 612), the method 600 may proceed from block 612 to block 614. Additionally, in response to the weather condition being between the minimum threshold and the maximum threshold ("Yes" at 614), the method 600 may proceed from block 614 to block 612.

In FIG. 6, the blocks 606, 608, and 610 may be included in or defined in an optimal biological state 620. Additionally, block 612 and block 614 may be included in or defined in an optimal environmental state 622, and the blocks 616 and 618 may be commands 624. Additionally still, blocks 606, 608, 610, 612, 614, 616, and 618 may be included in or defined in a policy 626. In some embodiments, the optimal biological state 620 may include more blocks that may include more thresholds of other biological conditions. Additionally or alternatively, the optimal environmental state 622 may include more blocks that may include more thresholds of other environmental conditions. Additionally or alternatively, the commands 624 may include more blocks with more commands.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include tangible or non-transitory computer-readable storage media including RAM, ROM, EEPROM, CD-ROM or other optical disk storage, magnetic disk storage or other magnetic storage devices, or any other non-transitory storage medium which may be used to carry or store desired program code in the form of computer-executable instructions or data structures and which may be accessed by a general-purpose or special-purpose computer. Combinations of the above may also be included within the scope of computer-readable media.

Computer-executable instructions comprise, for example, instructions and data, which cause a general-purpose computer, special-purpose computer, or special-purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" may refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modules running on a computing system.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present invention have been described in detail, it should be understood that the various changes, substitutions, and alterations could be made hereto without departing from the spirit and scope of the invention.

What is claimed is:

1. A method of dynamically adapting an environment, the method comprising:
    collecting sensor data from one or more biological sensors and one or more environmental sensors;
    removing noise from the sensor data;
    combining the sensor data from the one or more biological sensors with the sensor data from the one or more environmental sensors;
    based on the combined sensor data, computing an actual environmental state of an environment and an actual biological state of an individual in the environment;
    based on the computed actual environmental state and the actual biological state, determining whether an optimal environmental state exists in the environment and an optimal biological state of the individual exists, the optimal environmental state and the optimal biological state being defined in a health and wellness policy; and
    in response to the optimal environmental state not existing in the environment:
        identifying an environmental condition that differs from the optimal environmental state; and
        generating a command configured to alter an operational state of an environmental device that affects the environmental condition; and
        communicating the command to an environmental device regulator configured to control the environmental device.

2. The method of claim 1, further comprising:
    collecting updated sensor data from the one or more biological sensors and the one or more environmental sensors;
    determining whether the command placed the environment in the optimal environmental state; and
    in response to the command not having placed the environment in the optimal environmental state:
        identifying an updated environmental condition that differs from the optimal environmental state; and
        generating an updated command configured to alter a second operational state of a second environmental device that affects the updated environmental condition.

3. The method of claim 1, further comprising identifying a biological condition that deviates from a limit of an optimal biological condition of the optimal biological state defined in the health and wellness policy and that is influenced by the environmental condition.

4. The method of claim 1, wherein:
    the optimal environmental state includes limits for one or more environmental conditions configured to promote the optimal biological state of the individual while performing an activity in the environment; and
    the limits include one or more of weighted thresholds, Boolean combinations of limits, and optimal ranges for one or more environmental conditions.

5. The method of claim 1, wherein one or more of the collecting, the determining, the identifying, and the generating occur continuously.

6. The method of claim 1, wherein:
    the environment includes a sleep environment;
    the one or more biological sensors include one or more of an electroencephalography (EEG) sensor, a body temperature sensor, a galvanic skin response sensor, and a sleep activity sensor;
    the one or more environmental sensors include one or more of an ambient room temperature sensor, an ambient humidity sensor, an ambient light sensor, an ambient audio sensor, an ambient weather environmental sensor, and an ambient environmental allergy sensor; and
    the environmental device includes one or more of a humidifier and a heater.

7. The method of claim 1, wherein:
    the environment includes an ergonomic environment;
    the one or more biological sensors include one or more of an electrocardiography (ECG) sensor, an electromyography (EMG) sensor, and multiple accelerometers;
    the one or more environmental sensors includes one or more of a seat height sensor, a seat position sensor, a back tilt sensor, a knee tilt sensor, and a desk height sensor; and
    the environmental device includes one or more of a desk height actuator and a seat position actuator.

8. The method of claim 1, wherein:
    the environment includes a driving environment;
    the one or more biological sensors include one or more of an electrocardiography (ECG) sensor, a camera, and a driving quality sensor;
    the one or more environmental sensors includes one or more of a traffic site and weather sensors; and
    the environmental device includes one or more of an alarm and a heating, ventilation, and air conditioning (HVAC) component.

9. A non-transitory computer-readable medium having encoded therein programming code executable by a processor to perform operations comprising:
    collecting sensor data from one or more biological sensors and one or more environmental sensors;
    removing noise from the sensor data;
    combining the sensor data from the one or more biological sensors with the sensor data from the one or more environmental sensors;
    based on the combined sensor data, computing an actual environmental state of an environment and an actual biological state of an individual in the environment;

based on the computed actual environmental state and the actual biological state, determining whether an optimal environmental state exists in the environment and an optimal biological state of the individual exists, the optimal environmental state and the optimal biological state being defined in a health and wellness policy; and in response to the optimal environmental state not existing in the environment:

identifying an environmental condition that differs from the optimal environmental state; and generating a command configured to alter an operational state of an environmental device that affects the environmental condition; and communicating the command to an environmental device regulator configured to control the environmental device.

10. The non-transitory computer-readable medium of claim 9, wherein the operations further comprise:

collecting updated sensor data from the biological sensor and the environmental sensor;

determining whether the command placed the environment in the optimal environmental state; and in response to the command not having placed the environment in the optimal environmental state:

identifying an updated environmental condition that differs from the optimal environmental state; and generating an updated command configured to alter a second operational state of a second environmental device that affects the updated environmental condition.

11. The non-transitory computer-readable medium of claim 9, wherein the operations further comprise identifying a biological condition that deviates from a limit of an optimal biological condition of the optimal biological state defined in the health and wellness policy and that is influenced by the environmental condition.

12. The non-transitory computer-readable medium of claim 9, wherein:

the optimal environmental state includes limits for one or more environmental conditions configured to promote the optimal biological state of the individual while performing an activity in the environment; and the limits include one or more of weighted thresholds, Boolean combinations of limits, and optimal ranges for one or more environmental conditions.

13. The non-transitory computer-readable medium of claim 12, wherein one or more of the collecting, the determining, the identifying, and the generating occur continuously.

14. The non-transitory computer-readable medium of claim 9, wherein:

the environment includes a sleep environment;

the biological sensor includes one or more of an electroencephalography (EEG) sensor, a body temperature sensor, a galvanic skin response sensor, and a sleep activity sensor;

the environmental sensor includes one or more of an ambient room temperature sensor, a humidity sensor, a light sensor, an audio sensor, a weather environmental sensor, and an environmental allergy sensor; and the environmental device includes one or more of a humidifier and a heater.

15. The non-transitory computer-readable medium of claim 9, wherein:

the environment includes an ergonomic environment;

the biological sensor includes one or more of an electrocardiography (ECG) sensor, an electromyography (EMG) sensor, and multiple accelerometers;

the environmental sensor includes one or more of a seat height sensor, a seat position sensor, a back tilt sensor, a knee tilt sensor, and a desk height sensor; and the environmental device includes one or more of a desk height actuator and a seat position actuator.

16. The non-transitory computer-readable medium of claim 9, wherein:

the environment includes a driving environment;

the one or more biological sensors include one or more of an electrocardiography (ECG) sensor, a camera, and a driving quality sensor;

the one or more environmental sensors includes one or more of a traffic site and weather sensors; and the environmental device includes one or more of an alarm and a heating, ventilation, and air conditioning (HVAC) component.

* * * * *